United States Patent
Ianiro et al.

(10) Patent No.: US 9,173,916 B2
(45) Date of Patent: *Nov. 3, 2015

(54) METHOD OF PREPARING A MUSCADINE POMACE EXTRACT

(71) Applicant: Shaklee Corporation, Pleasanton, CA (US)

(72) Inventors: Teodoro T. Ianiro, Concord, CA (US); Laurel A. Fisher, San Francisco, CA (US); William J. Mergens, West Palm Beach, FL (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/828,707

(22) Filed: Mar. 14, 2013

(65) Prior Publication Data

US 2013/0202725 A1     Aug. 8, 2013

Related U.S. Application Data

(63) Continuation-in-part of application No. 13/056,536, filed as application No. PCT/US2009/052343 on Jul. 31, 2009, now Pat. No. 8,568,804, which is a continuation-in-part of application No. 13/056,559, filed as application No. PCT/US2009/052346 on Jul. 31, 2009, application No. 13/828,707, which is a continuation-in-part of application No. 13/784,566, filed on Mar. 4, 2013.

(60) Provisional application No. 61/085,369, filed on Jul. 31, 2008, provisional application No. 61/085,371, filed on Jul. 31, 2008.

(51) Int. Cl.
| | |
|---|---|
| *A61K 36/87* | (2006.01) |
| *A61K 31/065* | (2006.01) |
| *A61K 31/352* | (2006.01) |
| *A23L 1/30* | (2006.01) |
| *A61K 31/05* | (2006.01) |

(52) U.S. Cl.
CPC .............. *A61K 36/87* (2013.01); *A23L 1/3002* (2013.01); *A61K 31/05* (2013.01); *A61K 31/065* (2013.01); *A61K 31/352* (2013.01)

(58) Field of Classification Search
CPC ...................................................... A61K 36/87
USPC .......................................... 424/766, 777, 776
See application file for complete search history.

(56) References Cited

U.S. PATENT DOCUMENTS

| | | | |
|---|---|---|---|
| 6,190,716 B1 | 2/2001 | Galbreath, Jr. | |
| 6,638,545 B1 | 10/2003 | Rombi | |
| 8,017,147 B2 | 9/2011 | Mazed et al. | |
| 8,075,929 B2 | 12/2011 | Shrikhande et al. | |
| 8,114,445 B2 | 2/2012 | Hastings | |
| 8,173,181 B2 | 5/2012 | Ferguson et al. | |
| 8,182,849 B2 | 5/2012 | Endo et al. | |
| 8,512,771 B2 * | 8/2013 | Ianiro et al. .................... | 424/766 |
| 8,568,804 B2 * | 10/2013 | Fisher et al. .................. | 424/766 |
| 2004/0137094 A1 * | 7/2004 | Mower et al. ................. | 424/769 |
| 2004/0234671 A1 | 11/2004 | Ector et al. | |
| 2005/0158376 A1 | 7/2005 | Sardi et al. | |
| 2006/0024392 A1 | 2/2006 | Magnuson et al. | |
| 2006/0121137 A1 | 6/2006 | Hartle et al. | |
| 2006/0277887 A1 | 12/2006 | Dalton | |
| 2007/0003644 A1 | 1/2007 | Randhava et al. | |
| 2009/0176718 A1 | 7/2009 | Ribnicky et al. | |
| 2010/0004344 A1 | 1/2010 | Dallas | |
| 2011/0177182 A1 | 7/2011 | Ianiro et al. | |
| 2011/0177183 A1 | 7/2011 | Ianiro et al. | |

FOREIGN PATENT DOCUMENTS

| | | |
|---|---|---|
| CN | 1343100 A | 4/2002 |
| CN | 1698733 A | 11/2005 |
| CN | 1956733 A | 5/2007 |
| WO | WO 98/17250 A1 | 5/1997 |
| WO | WO 2005/099761 A1 | 10/2005 |
| WO | WO-2005-110404 A2 | 11/2005 |

(Continued)

OTHER PUBLICATIONS http://www.quackwatch.com/01QuackeryRelatedTopics/antiagingpp.html—accessed May 2014.*
Sikora (Experimental Gerontology (2013), vol. 48, pp. 661-666).*
http://thefreedictionary.com/pomace—accessed May 2014.*
Sistrunk (J. Amer. Soc. Hort. Sci. (1985), vol. 110, No. 3, pp. 328-332).*
Talcott (J. Agric. Food Chem (2002), vol. 50, pp. 3186-3192).*
Carroll (Am. J. Enol. Vitic. (1984), vol. 35, No. 2, pp. 72-74).*
Lamikanra (HortScience (1988), vol. 23, No. 3, pp. 597-599).*
Ector et al., "Resveratrol Concentration in Muscadine Berries, Juice, Pomace, Purees, Seeds and Wines," *Am. J. Enol. Vitic.*, vol. 47(1):57-62 (1996).

(Continued)

Primary Examiner — Susan Hoffman
(74) Attorney, Agent, or Firm — Klarquist Sparkman, LLP

(57) ABSTRACT

Muscadine grape extracts are disclosed that have antioxidant properties. The extracts are a mixture of extracts from bronze and purple muscadine grapes that unexpectedly increase the solubility of ellagic acid in the mixture. Solvent extracts are obtained in some examples by water extracting the pomaces of the grapes from which the juice has substantially been removed. Further surprising increases in ellagic acid solubility can also be obtained by adding an additional source of anthocyanins to the extract, for example by including in the composition an extract of whole purple muscadine grapes from which substantial amounts of the juice have not been removed. Other additional sources of anthocyanins include blueberries, blackberries and raspberries; the additional source of anthocyanins can be obtained from a fruit processing waste stream to increase the efficiency of the production process.

39 Claims, No Drawings

(56) References Cited

FOREIGN PATENT DOCUMENTS

WO    WO 2007/074472 A2    7/2007
WO    WO 2008/144019      11/2008

OTHER PUBLICATIONS

Soleas et al., "Comparative Evaluation of Four Methods for Assay of cis- and trans-Resveratrol," Am. J. Enol. Vitic., vol. 48(2):169-176 (1997).

Percival and Sims, "Wine Modifies the Effects of Alcohol on Immune Cells of Mice [1-3]," J. of Nutrition, vol. 130(5):1091-1094 (2000).

Chen et al., "High-speed counter-current chromatography separation and purification of resveratrol and piceid from Polygonum cuspidatum," J. of Chromatography A, vol. 907:343-346 (2001).

Pastrana-Bonilla et al., "Phenolic Content and Antioxidant Capacity of Muscadine Grapes," J. Agricultural and Food Chemistry, vol. 51:5497-5503 (2003).

Ke-lin "Impact of Grape Seed Extract on Human Health," China Drinks, pp. 46-47 (2003).

Mertens-Talcott et al. Low Concentrations of Quercetin and Ellagic Acid Synergistically Influence Proliferation, Cytotoxicity and Apoptosis in MOLT-4 Human Leukemia Cells [1-3], J. Nutrition 133:2669-2674 (2003).

Yilmaz and Toledo, "Major Flavonoids in Grape Seeds and Skins: Antioxidant Capacity of Catechin, Epicatechin, and Gallic Acid," J. Agric. Food. Chem., vol. 52:255-260 (2004).

Kurilich et al. "Plasma and Urine Responses Are Lower for Acylated vs. Nonacylated Anthocyanins from Raw and Cooked Purple Carrots," J. Agric. Food Chem. 53(16):6537-6542 (2005).

Mertens-Talcott et al. "Ellagic acid and quercetin interact synergistically with resveratrol in the induction of apoptosis and cause transient cell cycle arrest in human leukemia cells," Cancer Letters 218:141-151 (2005).

Dansby "Evaluation of the Antioxidant and Biological Properties of Muscadine Grape Seed Extracts," Dissertation North Carolina State University, pp. ii-v, 1, 45 (2006).

Xiao-jia et al. "Review on Health Function, Processing Technology and Determination of Resveratrol," Food Research and Development, vol. 27(2):123-126 (2006).

J. Ponce "Chemical and Economic Analysis of Value-added Product from Muscadine Grape Pomace," University of Florida http://ufdc.ufl.edu/UFE0021495/00001 (2007) *Not catalogued until Apr. 2, 2010.

God et al. "Anticancer Effects of Four Varieties of Muscadine Grapes," J. of Medical Food 10(1):54-59 (2007).

Hudson et al. "Inhibition of Prostate Cancer Growth by Muscadine Grape Skin Extract and Resveratrol through Distinct Mechanisms," Cancer Research 67(17):8396-8405 (2007).

Sapcanin et al. "Antioxidant Capacity in the Lipophilic Fraction of Alzheimer's Brain Tissues," Bosnian J. Basic Medical Sciences 7(4):317-321 (2007).

Perron and Brumaghim "A Review of the Antioxidant Mechanisms of Polyphenol Compounds Related to Iron Binding," Cell Biochem Biophys, 53:75-100 (2009).

Cardona et al. "Color and Polyphenolic Stability in Extracts Produced from Muscadine Grape (Vitis rotundifolia) Pomace," J. of Agriculture and Food Chemistry, vol. 57:8421-8425 (2009).

T. Vashisth "Evaluation of Drying Technologies for Muscadine Pomace to Produce an Antioxidant Rich Functional Food Ingredient," The University of Georgia http://hdl.handle.net/10724/11195 (2009).

Sandhu and Gu "Antioxidant Capacity, Phenolic Content, and Profiling of Phenolic Compounds in the Seeds, Skin, and Pulp of Vitis rotundifolia (Muscadine Grapes) As Determined by HPLC-DAD-ESI-MS", J. of Agriculture and Food Chemistry, vol. 58:4681-4692 (2010).

Ghanim et al. "A Resveratrol and Polyphenol Preparation Suppresses Oxidative and Inflammatory Stress Response to a High-Fat, High-Carbohydrate Meal," J. Clin. Endocrinol Metab., vol. 96(5):1409-1414 (2011).

Soto et al. "Recovery and Concentration of Antioxidants from Winery Wastes," Molecules 17:3008-3024 (2012).

\* cited by examiner

METHOD OF PREPARING A MUSCADINE POMACE EXTRACT

RELATED APPLICATIONS

This application is a continuation-in-part of U.S. application Ser. No. 13/056,536, filed Jan. 28, 2011, now U.S. Pat. No. 8,568,804, which is the §371 U.S. National Stage of International Application No. PCT/US2009/052343, filed on Jul. 31, 2009, which was published in English under PCT Article 21 (2), which in turn claims the benefit of and priority to U.S. Provisional Application No. 61/085,369 filed on Jul. 31, 2008, all of which applications are incorporated herein in their entirety.

This application is also a continuation-in-part of U.S. application Ser. No. 13/056,559, filed Jan. 28, 2011, now U.S. Pat. No. 8,512,771, which is the §371 U.S. National Stage of International Application No. PCT/US2009/052346, filed on Jul. 31, 2009, which was published in English under PCT Article 21 (2), which in turn claims the benefit of and priority to U.S. Provisional Application No. 61/085,371 filed on Jul. 31, 2008, all of which applications are incorporated herein in their entirety.

This application is also a continuation-in-part of U.S. application Ser. No. 13/784,566, filed Mar. 4, 2013, which is also incorporated by reference.

FIELD

This invention relates to methods for making an antioxidant composition that contains muscadine grape extract, and in particular extracts obtained from bronze and purple muscadine grapes.

BACKGROUND

Reactive oxygen species (ROS) are obligatory byproducts of aerobic metabolism and thus are generated continuously in humans and other organisms. Humans are also exposed to ROS from exogenous/environmental sources such as pollution, sunlight and diet. While there are different chemical forms of ROS, they all produce deleterious actions on the structure and function of cellular constituents and macromolecules. The intensity of ROS generation/exposure is termed oxidative stress.

Oxidative stress is considered to be associated with the pathogenesis of chronic inflammatory diseases such as diabetes, cancer, atherosclerosis and other cardiovascular diseases, as well as with degenerative neurological diseases such as Alzheimer's disease and Parkinson's disease. Moreover, multiple lines of evidence support the view that oxidative stress is a central mechanism underlying normal aging. Accordingly, a need exists to develop compositions and methods to inhibit oxidative stress.

The moderate use of wine has been reported to lower the incidence of cardiovascular diseases and their consequent mortality in wine-drinking populations. Moderate wine intake has also been reported to provide a neuroprotective effect against dementia. Grapes contain several bioactive polyphenolic compounds, including flavonoids (such as flavan-3-ols and oligomers thereof known as proanthocyanidins; flavonols, anthocyanins, and flavanones) and non-flavonoids (such as phenolic acids, tannins and stilbene derivatives, for example resveratrol). The non-flavonoid resveratrol has been considered to mediate many of the beneficial effects of grape products on the human cardiovascular system. The protective and anti-inflammatory effects of the flavonoids are believed to be due to free radical scavenging, various effects on cellular signaling pathways and gene expression, and selective interference with a multitude of factors that affect the cell division cycle of rapidly and abnormally proliferating mammalian cells.

SUMMARY

Methods and compositions are disclosed herein for producing a muscadine pomace solvent extract composition that contains a combination of bronze muscadine pomace extract and purple muscadine pomace extract. It has unexpectedly been found that the combination of the extracts from the different colored grapes desirably increases the ellagic acid solubility in the composition. It has also been found that the solubility of the ellagic acid can be further increased by including in the composition and/or extraction method an anthocyanin that is not obtained from an extract of the pomace-only. The anthocyanin can be obtained, for example, from the whole purple muscadine grapes or another colored fruit such as blueberry, blackberry, or raspberry, or a fruit processing waste stream. In other examples the anthocyanin is obtained from the juice or skins or both of such a colored fruit. In one particularly disclosed embodiment, bronze muscadine grape pomace-only and whole purple muscadine grapes (pomace plus juice) are solvent extracted either separately or together, for example with water, such that the combined extracts contain anthocyanins from the whole purple muscadine grape. In some embodiments the combined extract may then be combined with an extract of a purple muscadine pomace-only to produce the composition having unexpectedly increased ellagic acid solubility.

Hence in one embodiment of the method the purple muscadine pomace includes pomace contained in whole purple muscadine grapes, and the purple muscadine pomace extract comprises at least in part an extract from whole purple muscadine grapes. The purple muscadine pomace extract can therefore include a mixture of extract from (a) whole purple muscadine grapes; and (b) extract from the pomace-only portion of the purple muscadine grapes from which juice has previously been extracted. Alternatively, the muscadine grape extract can be solely from bronze and purple muscadine pomace-only wherein the pomace-only consists essentially of the pomace without the juice. In either case, the bronze muscadine pomace extract can be combined with the purple muscadine pomace extract (such as purple muscadine pomace-only extract) to produce muscadine pomace extract in which the bronze muscadine pomace extract and purple muscadine pomace extract are present in a ratio that ranges from 0.1 to 10 (weight to weight) and the muscadine pomace extract has a polyphenol content of at least 2%, for example about 4% or more. In more particular examples, the bronze muscadine pomace extract and purple muscadine pomace extract are present in a ratio that ranges from 0.3 to 3. In these ratios, the "pomace extract" includes extract from pomace-only and/or the pomace component of a whole grape.

The bronze and purple extracts can be produced either simultaneously or sequentially. In one example of simultaneous extraction, bronze muscadine pomace-only (without whole grapes) and whole purple muscadine grapes are combined and simultaneously solvent extracted to provide a mixed extract from (a) the bronze pomace-only and (b) an extract of the whole purple grape (which includes an extract of juice contained within whole purple grape and an extract of the pomace-only portion of the whole purple grape). Alternatively, bronze and purple muscadine pomace-only (without any bronze or purple whole grapes) are combined and simultaneously extracted. In yet another example, the bronze pomace-only, purple pomace-only and whole purple grapes are combined and all three are simultaneously extracted. In an example of sequential extraction, purple muscadine pomace from other than the whole grapes (for example pomace-only) and bronze muscadine pomace from other than the whole grapes (for example pomace-only) are separately extracted, and then those extracts are combined. In a further example of a sequential extraction, the combined purple/bronze extracts are then in turn combined with an extract from purple muscadine pomace (not whole grapes) or an extract from whole purple muscadine grapes, or a combination of an extract from whole purple grapes and an extract from bronze pomace (not whole grapes).

In some particularly disclosed embodiments, the bronze muscadine pomace extract and the purple muscadine pomace extract are prepared prior to combining the bronze muscadine pomace extract with the purple muscadine pomace extract to produce a muscadine pomace extract having a polyphenol content of at least 2%. For example, the bronze muscadine pomace and purple muscadine pomace are extracted with water to produce the bronze muscadine pomace extract and the purple muscadine pomace extract prior to combining the bronze muscadine pomace extract with the purple muscadine pomace extract to produce the muscadine pomace extract having a polyphenol content of at least 2%.

Preparing the bronze muscadine pomace extract and the purple muscadine pomace extract can further include filtering the bronze muscadine extract and purple muscadine extract either (a) separately prior to combining them or (b) together after combining them, to produce the muscadine extract having a polyphenol content of at least 2%. The bronze and purple pomace extracts may also be fermented either separately or in combination to help remove extracted sugars. Such fermentation may occur either before or after filtering the muscadine pomace extract.

The bronze and purple muscadine extracts may further be concentrated so that each extract comprises 20% to 50% solids in a liquid, for example about 40% solids in a liquid. In some examples the muscadine pomace extract is concentrated after filtering the muscadine pomace extract.

An excipient or additional ingredient can be added to the extract after extraction, for example to make an antioxidant composition. The additional ingredients may include resveratrol or anthocyanins. In one particular example, anthocyanins are added during extraction by extracting whole purple muscadine grapes to simultaneously extract the pomace of the grape and the anthocyanins that are present in the grape juice.

Compositions are also disclosed that are made by the foregoing or other methods. In particular examples, the ratio of bronze muscadine pomace extract to purple muscadine pomace extract in the composition is present in a ratio that ranges from 0.1 to 10 (weight to weight) and the muscadine pomace extract has a polyphenol content of at least 2%. These compositions can be administered to a subject in need of them to inhibit cellular aging by preventing or inhibiting one or more processes associated with cellular aging, such as free radical formation or activity. In some embodiments, the purple muscadine pomace extract includes (a) an extract of whole purple muscadine grapes; (b) an extract of purple muscadine pomace from other than whole grapes; or (c) a mixture of (a) and (b). The composition may be included in a non-beverage food, a beverage, a dietary supplement, a cosmetic composition, or an anti-aging supplement The compositions may be used in a method of inhibiting oxidative stress by administering to a subject in need thereof a dose of the composition sufficient to reduce or inhibit oxidative stress. In some embodiments, the dose is administered 10 to 30 minutes before or after meal consumption.

The muscadine composition can include resveratrol or an anthocyanin from a source other than muscadine pomace or muscadine grape in an antioxidant composition. For example, the composition can contain resveratrol from Japanese knotweed extract in an antioxidant composition or anthocyanin from a source other than muscadine pomace, such as the juice in whole purple muscadine grapes, or anthocyanins from another colored fruit such as blueberry, blackberry or raspberry added during the extraction process. In one embodiment, the anthocyanins can be from a fruit processing waste stream. For example, the waste stream anthocyanins can be from the skins of colored fruit after they have been processed to purees, jellies, jams, and fruit juice concentrates. The waste stream would be added during the extraction process and not subsequently added to the composition after the extraction process is complete. However, the end product antioxidant composition can also have additional anthocyanins (for example from elderberry extract) added to it.

In some examples, the muscadine pomace extract contains or is prepared by simultaneously extracting whole purple muscadine grapes and bronze muscadine pomace in a ratio that ranges from 1:5 to 1:12 (weight:weight), such as a ratio of whole purple muscadine grapes to bronze muscadine pomace of 1:7 (weight:weight) or 1:9 (weight:weight) or 1:10 (weight:weight). In another example, the muscadine pomace extract contains or is obtained by extracting (a) whole purple muscadine grapes and (b) a mixture of bronze and purple muscadine pomace in a ratio of (a) to (b) that ranges from 1:7 to 1:16 (weight:weight) such as 1:9 (weight:weight) or 1:12 (weight:weight). Alternatively, the muscadine pomace extract is prepared from whole purple muscadine grapes, purple muscadine pomace, and bronze muscadine pomace wherein the ratio in them of anthocyanins to ellagic acid ranges from 0.5:1 to 5:1 (weight:weight) such as 1:1 (weight:weight) or 1.3:1 (weight:weight).

The foregoing and other objects, features, and advantages of the invention will become more apparent from the following detailed description, which proceeds with reference to the accompanying figures.

DETAILED DESCRIPTION

I. Abbreviations and Terms (a) Abbreviations

FRAP: Ferric Reducing Ability of Plasma
mg: milligram
μg: microgram
ml: milliliter
ORAC: Oxygen Radical Absorbance Capacity
ROS: Reactive oxygen species
TE: Trolox Equivalent
TEAC: Trolox Equivalent Antioxidant Capacity
wt: weight (b) Terms The following explanations of terms and methods are provided to better describe the present disclosure and to guide those of ordinary skill in the art in the practice of the present disclosure. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. All percentages and ratios are calculated by weight unless otherwise indicated.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, transdermal, intranasal, topical and inhalation routes.

Anthocyanin: A water-soluble vacuolar pigment found in many plants that may appear red, purple or blue depending on the pH. Anthocyanins belong to a parent class of molecules called flavonoids that are synthesized via a phenylpropanoid pathway. Anthocyanins have the general chemical structure shown below:

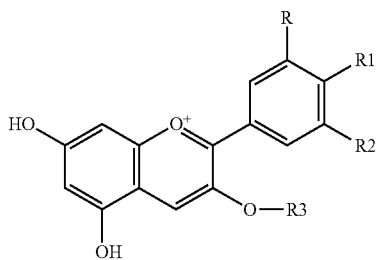

Chemical structure of anthocyanins

"Anthocyanins from a source other than muscadine" refers to anthocyanins obtained from a source other than a muscadine grape. Examples of such non-muscadine sources include elderberry, black currant fruit, blueberry, black raspberry, red raspberry, bilberry, grape or purple carrot.

Antioxidant activity: Activity that reduces oxidative stress, for example by scavenging and neutralizing oxidative free radicals. Antioxidant activity can be measured using the methods disclosed herein as well as those known in the art, including the Oxygen Radical Absorbance Capacity (ORAC) assay, the Ferric Reducing Ability of Plasma (FRAP) assay, and the Trolox Equivalent Antioxidant Capacity (TEAC) assay. For example, a composition has antioxidant activity and can be used as an antioxidant if it has a total ORAC of at least 24 μmole Trolox Equivalents per mg polyphenol (μmoleTE/mg polyphenol).

Antioxidant composition: A composition that has antioxidant activity.

Antioxidative effective amount: An amount sufficient to induce an antioxidant effect in a subject to whom the amount of a composition is administered. In some examples, the composition induces a selectively synergistic increase in $ORAC_{lipophilic}$ antioxidant activity by increasing $ORAC_{lipophilic}$ to a greater extent than what would be predicted from the addition of the $ORAC_{lipophilic}$ values of the individual components of the composition.

Elderberry (*Sambucus nigra*): A plant belonging to the Adoxaceae family found in Europe and North America with several regional varieties or subspecies. The flowers are in flat corymbs. The berries are black to glaucous blue and contain anthocyanins and other polyphenolics (for example, proanthocyanidins and flavonols such as quercetin) in which the amount and type of anthocyanins and other polyphenolics vary depending upon the variety.

An "elderberry extract" is a material obtained by extracting an elderberry according to any extraction method known to one of skill in the art, so long as it has the desired activity (e.g., color stabilizing activity, antioxidant activity or a combination thereof). For example, the elderberry extract can include a fruit juice obtained by compressing elderberry fruit, or an extract obtained by extracting whole fruit of elderberry or a suitable portion of skin or seed of the fruit according to known extraction methods, such as solvent (for example water) extraction. Also, a crushed product of an elderberry fruit or a dried elderberry fruit concentrate can be used as "an elderberry extract."

Excipient: An inactive substance used as a carrier for the active ingredients of a composition. Excipients can include substances that are used as bulk in formulations with very potent active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In a particular example, the disclosed anti-aging supplement includes the following excipients: glycerin, sorbitol, colloidal silicon dioxide, and a natural flavoring additive.

Extract: To separate a substance from a matrix. An extract is also the substance made by extracting a part of a raw material, for example by using pressure or a solvent such as ethanol and/or water. Extracts may be in liquid or powder form. Particular examples of extracts disclosed herein are in liquid form. A "solvent extract" refers to an extract obtained by exposing a target to a liquid solvent that solubilizes the desired substance contained in a product. A "water extract" is an extract obtained by water extraction of a product. Solvent extracts remove target substances from the product according to the solubility of the target substance in the solvent.

Inhibiting (including preventing) cellular aging: Inhibiting (for example preventing) one or more processes associated with cellular aging, such as inhibiting free radical formation or activity in a subject who ingests the composition. Preventing cellular aging refers to an intervention that ameliorates a sign or symptom of cellular aging. Preventing includes prophylaxis to delay the onset of one or more processes associated with cellular aging. Prevention or inhibition of cellular aging does not require a total absence of cellular aging. In a particular example, a disclosed composition decreases or delays a process associated with cellular aging by at least 10%, at least 20%, at least 50%, or even at least 90%. Such decreases can be measured using the methods disclosed herein as well as those known in the art.

Japanese Knotweed (*Fallopia japonica, Polygonum cuspidatum*): a large herbaceous perennial plant which is native to Eastern Asia in Japan, China and Korea. It is a concentrated source of resveratrol and its glucoside piceid (up to 0.05 to 0.2% of fresh weight).

Muscadine Grape (*Vitus rotundifolia*): Grapes native to the southeastern United States, and found in the wild from Delaware to the Gulf of Mexico and westward to Missouri, Kansas, Oklahoma, and Texas. Muscadines are well adapted to the warm, humid conditions of the southeastern United States. The fruit is borne in small, loose clusters of 3-40 grapes, quite unlike the large, tight bunches characteristic of European and American grapes. The round, 1 to 1½ inch fruits have a thick, tough skin and contain up to 5 hard, oblong seeds. In color the fruits range from greenish bronze through bronze, pinkish red, purple and almost black.

Many different varieties of muscadine grapes are available, including female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling.

For example the bronze colored varieties of muscadine grapes are identified by those skilled in the art as including Carlos, Chowan, Doreen, Higgins, Magnolia, Nevermiss, Pamlico, Roanoke, Scuppernong, Sterling, and Summit cultivars. Purple varieties are darker skinned then the bronze colored varieties and include Albermarle, Bountiful, Cowart, GA-1, Hunt, NC-1, Noble, Regale, Tarheel, and Jumbo. Some of the purple varieties are also referred to as Black colored.

The phytochemical constituents of the whole muscadine grape differ from *Vitis vinifera*. Muscadines have a higher total phenolic content distinguished by high ellagic, gallic, and flavonoid glycoside concentrations. The presence of ellagic acid in muscadine grapes is unique and is found in the form of free ellagic acid, ellagic acid glycosides, methoxylated derivatives and ellagitannins. Another unique feature is the anthocyanin chemistries observed in muscadines. Present as 3,5-diglucosides (as opposed to 3-glucosides) of delphinidin, cyanidin, petunidin, peonidin, and malvidin in non-acylated forms, these compounds and the natural color influence from other anthocyanins present within the grape impart a dark purple color to juice and pomace obtained from the purple varieties. Purple pomace extracts contain anthocyanins while bronze pomace extracts do not.

The red and purple colored anthocyanins found in purple muscadine grapes are polyphenolic compounds that have antioxidant properties. Purple and bronze muscadine grapes contain several other flavonoid classes of polyphenols with flavan-3-ols and their oligomers being the most abundant class and flavonols being the second most abundant flavonoids present in whole muscadines. The major phenolics reported for the muscadine skin fraction (in descending order) are ellagic acid, myricetin, quercetin, and kaempferol while those reported for seeds are epicatechin, catechin and gallic acid (Pastrana-Bonilla et al. *J. Agric. Food Chem.* 51:5497-5503, 2003).

A muscadine grape contains pomace and juice. "Other than the whole grape" includes a muscadine grape from which at least some of the juice has been extracted, and in some examples includes less than 95% or 90% of the original juice in the grape.

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more compositions, such as one or more muscadine compositions, and additional pharmaceutical agents.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions can contain minor amounts of non-toxic auxiliary substances, such as wetting or emulsifying agents, preservatives, and pH buffering agents and the like, for example sodium acetate or sorbitan monolaurate.

Polyphenols (also known as polyhydroxyphenols, phenolics and polyphenolics): A class of organic compounds characterized by the presence of multiple phenol structural units. Many of them are derived from plants, and can generally be divided into flavonoids, phenolic acids and stilbenes although there are multiple subclasses of flavonoids and phenolic acids. Polyphenols found in plants are usually complex mixtures of different polyphenol classes and moreover may be conjugated to sugar groups (polyphenol glycosides) or may occur in the aglycone form (without sugar group attachments). "Polyphenols from a source other than muscadine" refers to polyphenols that are present in or obtained from a product other than a muscadine grape and includes multiple classes of polyphenols such as flavonoids, tannins and phenolic acids. Examples of such non-muscadine sources include elderberry, black currant, blueberry, black raspberry, red raspberry, blackberry, bilberry, cloudberry, chokeberry, gooseberry, pomegranate, grape or purple carrot.

Pomace: The skins, seeds, and pulp remaining following juice extraction. In one example a pomace extract is a bronze muscadine pomace extract, a purple muscadine pomace extract or a combination thereof. Many different varieties of muscadine grape pomaces are available as starting materials, and they include female (pistillate) varieties such as Black Beauty, Black Fry, Darlene, Fry, Higgins, Jumbo, Scuppernong, Sugargate, Summit, Supreme, and Sweet Jenny, and self-fertile varieties such as Carlos, Cowart, Dixieland, Dixie Red, Fry Seedless, Magnolia, Nesbitt, Noble, Redgate, Regale and Sterling. Muscadine pomace contains phenolic compounds, including gallic acid and ellagic acid, having antioxidant properties.

The pomace can be present in a whole grape wherein the whole grape contains at least 90 or 95% of the juice of the grape, or the pomace can be substantially isolated and consist essentially only of the pomace once the grape has been compressed to remove the juice.

Pomace-only: The pomace portion of a grape from which juice has been removed, for example by compression of the grape. As used herein, "pomace-only" refers to a pomace that contains no more than 1% juice as a percentage of its weight. In some embodiments the pomace-only contains no more than 0.5% juice as a percentage of its weight.

Purified: The term purified does not require absolute purity; rather, it is intended as a relative term. Thus, for example, a purified substance is one in which the substance is more enriched than the substance in its natural environment, for example in a fruit (e.g., grape). In one embodiment, a preparation is purified such that the substance represents at least about 5% (such as, but not limited to, at least 10%, 20%, 30%, 40%, 50%, 70%, 80%, 90%, 95%, 98% or 99%) of the total content of the preparation. In an example, a disclosed composition with antioxidant activity includes trans-resveratrol with a minimum purity of at least 50%, 70%, 80%, 90%, 95%, 98% or 99% of the total resveratrol preparation (by weight). In one example, a "purified pomace" is a pomace in a grape from which some or substantially all of the juice has been removed.

Purple carrot (*Daucus carota*): a cultivar of carrot containing anthocyanin pigments. A "purple carrot extract" can be obtained by extracting a purple carrot according to any extraction method known in the art, such as pressing or solvent extractions, so long as the extract has the desired activity (e.g., color stabilizing activity, antioxidant activity or a combination thereof). In an example, a purple carrot extract has the property of stabilizing muscadine color pigment and can therefore be subsequently utilized as color-stabilizing additive.

Resveratrol: A phytoalexin that is a stilbenoid, a derivate of stilbene, and is produced in plants with the help of the enzyme stilbene synthase. Resveratrol exists as two structural isomers: cis- and trans-resveratrol. Trans-resveratrol can undergo isomerisation to the cis-form when heated or exposed to ultraviolet irradiation.

Resveratrol is found in widely varying trace amounts, on average it is less than 0.0001% (of fresh weight) when measured in grapes, raspberries, mulberries, plums, peanuts, berries of Vaccinium species, including blueberries, bilberries, and cranberries, and some pines, such as Scots pine and eastern white pine; the richest natural sources of resveratrol aglycone (up to 0.05% of fresh weight) are the roots and stalks of giant knotweed and Japanese knotweed. In grapes, any resveratrol present is found primarily in the skin and seeds. The amount of resveratrol found in grape skins varies with the grape cultivar, its geographic origin, and exposure to fungal infection. However, as noted above, it is typically present in only trace amounts.

As used herein, the term resveratrol can include natural trans-resveratrol extracted from a plant, such as grapes, or synthetic trans-resveratrol. As used herein, the term resveratrol can include modified formulations of trans-resveratrol such as microencapsulated or water dispersible forms.

"Resveratrol from a source other than muscadine" refers to resveratrol that is present in or obtained from a product other than a muscadine grape (or any subcomponent of the muscadine grape, such as its seeds). Resveratrol is substantially absent from solvent-extracted (such as water-extracted) muscadine pomace, and in some disclosed examples the muscadine pomace solvent extract is substantially free from resveratrol until the resveratrol from another source is added to the extract.

Subject: Living multi-cellular vertebrate organisms, a category that includes both human and veterinary subjects, such as a companion animal, including a cat, dog or horse. A "subject in need of an increase in mitochondrial biogenesis and/or antioxidant activity" is a subject who may benefit from such an increase, such as a subject who desires to decrease signs of age, offset tissue damage caused by oxidation, and/or improve cardiovascular, neurological, tumor-related, skin-appearance or other conditions that are associated with oxidative stress.

Therapeutically Effective Amount: An amount of a composition that alone, or together with an additional agent(s) (for example additional antioxidants), induces the desired response (e.g., prevents or inhibits cellular aging). The preparations disclosed herein can be administered in therapeutically effective amounts.

Whole-grape: A grape as it is found in nature, or which has been slightly compressed for example by a shipping process. A "whole grape" contains the pomace and at least 90% (for example 95%) of the original juice content.

II. Description of Several Embodiments

Plant agents have been studied extensively as a potential source of nutriceutical agents that can be used to reduce oxidative stress. Red grapes are among the many foods that have been the subject of intense research. The antioxidant effects of red grapes have been widely attributed to the polyphenolic compounds, such as resveratrol and procyanidins, the latter which appear in substantial quantities in the grapes.

A problem with the use of some muscadine pomace extracts in the past was that the solubility of ellagic acid in the extract was undesirably low, particularly in a bronze extract. As shown in WO 2010/014870 and WO 2010/014873, the inventors developed a method to promote the solubility of ellagic acid in a muscadine pomace extract by combining a bronze and purple muscadine pomace extract. The combination of bronze and purple muscadine pomace extract was found to surprisingly increase the solubility of ellagic acid in the combined extract. The solubility of ellagic acid solubility was surprisingly increased even at low ratios of purple to bronze extract (such as a ratio in the range of 0.1 to 10 or 0.3 to 3) in both unconcentrated and concentrated forms. Compositions that contained increased levels of ellagic acid in combination with supplemental resveratrol (from a source other than muscadine) were found to have surprisingly synergistic lipophilic antioxidant activity, particularly as measured by ORAC. The synergistic antioxidant activity in the lipophilic ORAC ($ORAC_{lipophilic}$) suggested that the antioxidant activity would be particularly effective in lipophilic environments, such as that found in low density lipoprotein (LDL). In particular examples, the exogenous source of resveratrol was Japanese knotweed extract.

It has also been determined that further synergistic effects can be obtained by combining resveratrol with a mixture of muscadine pomace extract and an additional source of polyphenols, such as a source of anthocyanins, for example elderberry fruit. See U.S. application Ser. No. 13/784,566 filed Mar. 4, 2013.

A. Increased Solubility of Ellagic Acid in Combined Bronze and Purple Muscadine Pomace Extracts Determination of the maximum solubility of ellagic acid (which is unique to muscadine grapes) in a muscadine pomace extract allowed extracts to be prepared with enhanced ellagic acid solubility (and thus capture the polyphenol profile of the pomace) which in turn allowed extracts with improved antioxidant activity to be prepared. As disclosed in WO 2010/014870 and WO 2010/014873 (which are incorporated herein by reference), muscadine extracts with improved ellagic acid solubility can be administered either alone or in combination with other compounds in a non-beverage food, a beverage, dietary supplement or a topical ointment. Various methods of making the combined extracts were disclosed, such as combining a bronze muscadine pomace extract with a purple muscadine pomace extract to produce a muscadine pomace extract, wherein the ratio of bronze muscadine pomace extract to purple muscadine pomace extract ranges from 0.1 to 10 (weight to weight), such as 0.3 to 3 (weight to weight). The combined extract could be extracted by separate extraction of bronze and purple muscadine grapes with subsequent combination of the extracts, or by simultaneous extraction of bronze and purple muscadine grapes combined in desired ratios.

In WO 2010/014870 and WO 2010/014873 the inventors determined the antioxidant capacity of the disclosed muscadine pomace extract and a Japanese knotweed extract, standardized to 98% trans-resveratrol, separately and in combination (in either a mixture or dietary supplement) as measured by an ORAC assay. Both hydrophilic antioxidant capacity and lipophilic antioxidant capacity of the samples were measured. These studies demonstrated a strong synergistic lipophilic antioxidant effect of a mixture of the muscadine pomace extract and Japanese knotweed root extract, standardized to 98% trans-resveratrol. The selective synergy exhibited in the lipophilic conditions was unexpected. The muscadine extract utilized in the composition can be a natural extract and can vary by species and extraction process while retaining synergistic lipophilic antioxidant activity. In particular examples specifically disclosed ratios of muscadine polyphenols to resveratrol are present in the composition.

A composition containing Japanese knotweed extract, standardized to 98% trans-resveratrol, in combination with a muscadine pomace extract has improved lipophilic antioxidant capacity when compared to the sum of the lipophilic antioxidant capacities contributed by the individual extracts contained in the composition. Oxidative processes occurring in lipophilic environments are thought to initiate the pathogenesis of many disease states, such as low density lipoprotein (LDL) oxidation in atherosclerosis and obesity-induced insulin resistance in Type II diabetes. Moreover, oxidation of dietary lipids within the gastrointestinal tract leads to absorption of cytotoxic and genotoxic lipid peroxidation products such as malondialdehyde (MDA). Lipophilic antioxidants have been found to be effective in reducing various types of skin damage by inhibiting lipid peroxidation and the products produced by lipid peroxidation, such as cross-linking agents. Since oxidative stress is a central mechanism underlying normal aging, the disclosed antioxidant compositions are useful for inhibiting free radical production or activity, thereby slowing processes associated with cellular aging.

The applicant's incorporated WO 2010/014870 and WO 2010/014873 disclose muscadine pomace extract compositions having improved antioxidant activity. The muscadine pomace extract compositions were disclosed as components of a non-beverage food, a beverage, a liquid or solid dietary supplement or a topical ointment. Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine polyphenols to trans-resveratrol is in the range of 0.1/1 to 10/1 (weight to weight). Methods of producing the disclosed compositions include combining a muscadine (*Vitis rotundifolia*) pomace extract having a polyphenol content of at least 2% and trans-resveratrol from a source other than muscadine with a minimum purity of at least 5%, wherein a ratio of muscadine pomace extract to trans-resveratrol is in the range of 0.2/1 to 50/1 (weight to weight), such as 5/1 to 50/1 (weight to weight) including 20/1 to 50/1 (weight to weight), such as 18 to 1 (weight to weight), thereby producing a muscadine pomace extract and trans-resveratrol mixture with antioxidant activity. In some embodiments, the ratio of bronze to purple muscadine pomace extract ranges from 0.1 to 10, such as 0.3 to 3, as described in further detail below.

B. Muscadine Pomace Extracts

Muscadine pomace extracts disclosed in WO 2010/014870 and WO 2010/014873 are derived from bronze muscadine pomace and purple muscadine pomace. In some embodiments, the ratio of bronze muscadine pomace extract to purple muscadine pomace extract in the muscadine pomace extract range from 0.1 to 10 (weight to weight), such as 0.3 to 3 (weight to weight). For example, the ratio of bronze muscadine pomace extract to purple muscadine pomace extract is about 2.75 to about 1 (weight to weight), 2.5 to about 1 (weight to weight), about 2.25 to about 1 (weight to weight), about 2 to about 1 (weight to weight), about 1.5 to about 1 (weight to weight), or about 1 to about 1 (weight to weight). In other examples, the ratio is about 10 to about 1, about 7.5 to about 1, or about 5 to about 1. As used herein the term "about" is defined as ±0.5. In a particular example, the ratio of bronze muscadine pomace extract to purple muscadine pomace extract is about 2.25 to about 1 (weight to weight).

In certain embodiments, the muscadine (*Vitis rotundifolia*) pomace extract has a polyphenol content of at least 2%. For example, the polyphenol content is at least 3%, at least 3.5%, at least 4%, at least 4.5%, at least 5%, at least 6%, at least 8%, at least 10%, at least 12%, or at least 14%. In a particular example, the muscadine (*Vitis rotundifolia*) pomace extract has a polyphenol content of about 4%.

In some embodiments, the disclosed muscadine pomace extracts include 20% to 50% solids, such as at least 25%, at least 30%, at least 35%, at least 37%, at least 40%, at least 42%, at least 44%, at least 46% or at least 48%, in a liquid. In a particular example, the extract includes about 40% solids in a liquid.

The muscadine pomace can be extracted while either present in a whole grape or from purified pomace that is substantially free of grape juice. In particular examples, the purified pomace is the skin seeds and pulp remaining after at least 50% of juice in the grape has been removed. In other examples, the purified pomace is the skin, seeds and pulp remaining after at least 60%, 70%, 80% or 90% of the juice has been removed from the grape, such that the pomace consists essentially of only the skin, seeds and pulp.

Extracts prepared from grape pomace contained in the whole grape have the advantage of containing extracted components from both the grape pomace and the grape juice. Purple muscadine grapes contain anthocyanins in their juice such that solvent extraction of the purple grape provides an extract that contains additional amounts of anthocyanins that contribute to the ability of the purple muscadine extract to solubilize ellagic acid in the combined bronze and purple muscadine grape extracts.

C. Methods of Making Muscadine Pomace Extracts

WO 2010/014870 and WO 2010/014873 also disclose methods of making muscadine pomace extracts wherein the ratio of bronze muscadine pomace extract to purple muscadine pomace extract ranges from 0.1 to 10 (weight to weight), such as 0.3 to 3 (weight to weight). Although the extracts can be obtained by any extraction method, such as pressing under pressure or extracting with a solvent, particular examples are solvent extracted, for example with alcohol, water (such as heated water), or a combination of alcohol and water. In one disclosed embodiment, muscadine pomace extracts are prepared by simultaneously extracting bronze muscadine pomace and purple muscadine pomace that are present in proportions that yield desired ratios of bronze and purple extract. In other examples, the bronze muscadine pomace extracts and purple muscadine pomace extracts are prepared separately. For example, bronze muscadine pomace and purple muscadine pomace are separately extracted with water, preferably heated water.

The extract can further be fermented to remove extracted sugars. In one example, fermentation is performed following extracting the bronze muscadine pomace and purple muscadine pomace but prior to combining the bronze muscadine pomace extract with the purple muscadine pomace extract to produce a disclosed muscadine pomace extract. In other examples, fermentation is performed after combining the bronze muscadine pomace extract with purple muscadine pomace extract in the desired post extraction ratio (such as at about a 2:25 to 1 bronze to purple ratio).

Fermentation may be performed by any method known to one of skill in art, including those described herein. For example, yeast and yeast nutrients can be added to the pomace and fermentation continued until the residual sugar content is converted to ethanol. In one example, two pounds of yeast are added per 1000 gallons of 1× (unconcentrated) extract; fermentation is typically complete after three days. In other examples, the amount and/or strain of yeast and duration and temperature of fermentation may vary according to individual methods known to one of skill in art. In some examples, enzymes are used to clarify and/or settle residues or to improve extraction yield in the pomace extracts. Examples of such enzymes include pectinase or a blend of enzymes from *Aspergillus niger* that are commercially available from sources such as Scott Laboratories. These enzymes may be added to the pomace extract before or during fermentation.

In some embodiments, the bronze muscadine pomace extracts and purple muscadine pomace extracts are filtered prior to and/or following fermentation. Filtration can be performed according to general methods known to those of skill in the art. In a particular example, extracts are filtered through sieves of appropriate mesh size, such as USP mesh (typically 120 mesh) or a similar cloth filter (for example filters commercially available from Millipore Corporation).

In certain embodiments, methods of making muscadine pomace extracts further include concentrating the bronze muscadine pomace extract and the purple muscadine pomace extract so that each extract includes 20% to 50% solids, such as at least 25%, at least 30%, at least 35%, at least 37%, at least 40%, at least 42%, at least 44%, at least 46% or at least 48%, in a liquid. In a particular example, the extracts are concentrated so that each extract includes about 40% solids in a liquid. Generally known methods for concentrating samples, including methods for concentrating samples disclosed herein, can be used to concentrate the bronze and purple extracts.

In a particular example, to prepare a muscadine pomace extract at 40% solids, the muscadine pomace extract is dried down into a powder form and re-constituted in water at 40% solids level. Alternatively, a more acceptable commercially approach is concentration by removal of the extraction solvent through evaporation under vacuum using a batch or continuous process. Batch processes involve placing the extract in a vessel under a vacuum of 20-29" of mercury while heating the vessel jacket to provide energy to increase the vapor pressure of the solvent. Solvent vapors are condensed external to the vessel and the rate of condensation controls the temperature of the condensate. The same principles apply to a continuous evaporation process but with the advantage that the condensate is exposed to elevated temperatures for a shortened period of time. Both processes are applicable to the concentration of a muscadine pomace extract described herein.

In particular embodiments, bronze and purple pomace are extracted separately and each of the extracts is filtered prior to combining the bronze and purple pomace extract at the desired ratio. In some examples, this method can further include fermenting the combined muscadine pomace extract to remove extracted sugars. In one example, more than one filtering step is used, for example by filtering the extract prior to and following fermentation. In some examples, the method can further include concentrating the extract, as described herein. For example, the extract is concentrated by removal of the extraction solvent through evaporation under vacuum.

In any of the foregoing examples of extraction methods, whole purple grapes can be substituted for purple pomace. The purple muscadine pomace extract can include (a) an extract of whole purple muscadine grapes; (b) an extract of purple muscadine pomace from other than whole grapes; or (c) a mixture of (a) and (b). The whole purple grapes contain grape juice that is a source of anthocyanins from other than the grape pomace, and when solvent extracted from the whole grape these anthocyanins have now been found to surprisingly enhance solubility of ellagic acid in the mixture of bronze and purple muscadine grape extracts. However, additional sources of anthocyanins can also be provided by a colored fruit or a byproduct of a colored fruit other than purple muscadine grapes, such as a blueberry, blackberry or raspberry. In other examples, the anthocyanin is from a product of a fruit processing stream such as a juice concentrate or a by-product of a fruit processing stream such as fruit skins that are separated from a fruit puree processing stream.

In some embodiments of the extraction method the muscadine pomace extract is produced by simultaneously extracting whole purple muscadine grapes and bronze muscadine pomace in a ratio that ranges from 1:5 to 1:12 (weight:weight). In other examples, an extract is produced that contains an extract of (a) whole purple muscadine grapes and (b) a mixture of bronze and purple muscadine pomace in a ratio of (a) to (b) that ranges from 1:7 to 1:16 (weight:weight). In other embodiments, the muscadine pomace extract is derived from whole purple muscadine grapes, bronze muscadine pomace and purple muscadine pomace in any combination wherein the ratio of anthocyanin to ellagic acid ranges from 0.5:1 to 5:1 (weight:weight).

D. Compositions with Antioxidant Activity

Disclosed herein are compositions with improved antioxidant activity. In some disclosed embodiments, the compositions includes a muscadine (*Vitis rotundifolia*) pomace extract having a polyphenol content of at least 2% and trans-resveratrol from a source other than muscadine grapes (such as a Japanese knotweed root extract) with a minimum purity of at least 5%, wherein a ratio of muscadine polyphenols to trans-resveratrol is in the range of 0.1/1 to 10/1 (weight to weight), thereby providing a composition with antioxidant activity.

In some examples, the composition includes a muscadine (*Vitis rotundifolia*) pomace extract having a total polyphenol content of at least 3%, at least 3.5%, at least 4%, at least 4.5%, at least 5%, at least 6%, at least 8%, at least 10%, at least 12% or at least 14% and trans-resveratrol from a source other than muscadine grapes with a minimum purity of at least 5%, at least 10%, at least 25%, at least 50%, at least 60%, at least 70%, at least 75%, at least 80%, at least 85%, at least 90%, at least 95%, at least 97%, or at least 98%. In a particular example, the composition includes a muscadine (*Vitis rotundifolia*) pomace extract with a polyphenol content of about 4% and trans-resveratrol from a source other than muscadine grapes with a minimum purity of at least 98%.

In some embodiments, the composition includes a muscadine pomace extract with 20% to 50% solids, such as at least 23%, at least 25%, at least 30%, at least 35%, at least 37%, at least 40%, at least 42%, at least 44%, at least 46% or at least 48%, in a liquid. In a particular example, the extract includes about 40% solids in a liquid.

In other embodiments, the resveratrol includes at least 5% trans-resveratrol, such as at least 10% trans-resveratrol, at least 20% trans-resveratrol, at least 30% trans-resveratrol, at least 40% trans-resveratrol, at least 50% trans-resveratrol, at least 55%, at least 60%, at least 70%, at least 75%, at least 80%, at least 85%, at least 90%, at least 95%, at least 97%, or at least 98% trans-resveratrol. In particular embodiments, resveratrol includes at least 50% trans-resveratrol, such as at least 55%, at least 60%, at least 70%, at least 75%, at least 80%, at least 85%, at least 90%, at least 95%, at least 97%, or at least 98% trans-resveratrol extracted from Japanese Knotweed (*Polygonum cuspidatum*) root. It is contemplated that other trans-resveratrol sources can be used in the disclosed composition including synthetic trans-resveratrol.

In certain embodiments, the disclosed antioxidant composition has a ratio of muscadine polyphenols to trans-resveratrol of at least 0.1 to 1 (weight to weight), such as, 0.25 to 1, 0.5 to 1, 0.6 to 1, 0.65 to 1, 0.7 to 1, 0.75 to 1, 0.8 to 1, 0.9 to 1 or 1 to 1 (weight to weight). In other embodiments, the ratio of muscadine polyphenols to trans-resveratrol may be as high as 10 to 1 (weight to weight), such as 2 to 1, 3 to 1, 4 to 1, 5 to 1, 7.5 to 1 or 9 to 1 (weight to weight). In a particular example the disclosed antioxidant composition has a ratio of muscadine polyphenols to trans-resveratrol of 0.75 to 1 (weight to weight).

In certain embodiments, the disclosed antioxidant composition has a ratio of muscadine pomace extract to trans-resveratrol ranging from 0.2/1 to 50/1 (weight to weight), such as 0.5 to 1, 1 to 1, 5 to 1, 10 to 1, 15 to 1, 20 to 1, 22 to 1, 25 to 1, 30 to 1, to 1, 40 to 1, or 45 to 1 (weight to weight).

In some embodiments, the disclosed compositions with antioxidant activity have a total ORAC of at least 21 μmole Trolox Equivalents per mg polyphenol (μmoleTE/mg polyphenol), such as at least 22 μmoleTE/mg polyphenol), at least 24 μmoleTE/mg polyphenol), at least 26 μmole μmoleTE/mg polyphenol, at least 28 μmoleTE/mg polyphenol, or at least 30 μmoleTE/mg polyphenol. In one example, a disclosed composition has a total ORAC of 24 μmoleTE/mg polyphenol.

Some examples of the disclosed compositions further include an elderberry extract, a purple carrot extract, an excipient (such as glycerin, sorbitol, colloidal silicon dioxide, or a natural flavoring additive) or a combination thereof. For example, the elderberry extract and purple carrot extract can be included to provide color to the composition or for additional antioxidant activity.

In other embodiments of the method, the antioxidant composition is further combined with polyphenols (such as anthocyanins) from a source other than muscadine, for example by adding elderberry fruit extract to the antioxidant composition. In particular embodiments the components are combined so that the antioxidant composition includes at least 10% polyphenols, for example up to 35% polyphenols, such as 12-32%. In particular disclosed examples, in which an elderberry extract is providing polyphenols such as anthocyanins, the elderberry extract provides at least one-fourth of the total polyphenols in the muscadine/elderberry mixture, for example one-third to two-thirds of the total polyphenols and at least one fifth, for example 25% to 90% of the anthocyanins in the muscadine/elderberry mixture.

Any of the disclosed compositions can be provided in a non-beverage food, a beverage, or a liquid or solid dietary supplement. In some examples, the disclosed compositions are provided as a beverage. The compositions herein (particularly the food, beverage and dietary supplement compositions) can be fortified with one or more nutrients, especially one or more vitamins and/or minerals. Non-limiting examples of such vitamins and minerals include iron, zinc, copper, calcium, phosphorous, niacin, thiamin, folic acid, pantothenic acid, iodine, vitamin A, vitamin C, vitamin B2, vitamin B3, vitamin B6, vitamin B12, vitamin D, vitamin E, and vitamin K. Commercially available sources of the vitamins and minerals may also be included in the present compositions.

In some examples, food and beverage compositions can also include one or more dietary fibers. By "dietary fiber" is meant complex carbohydrates resistant to digestion by mammalian enzymes, such as the carbohydrates found in plant cell walls and seaweed or produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose or cellulose flour can also be used. Naturally occurring fibers include fiber from whole citrus peel, citrus albedo, sugar beets, citrus pulp and vesicle solids, apples, apricots, and watermelon rinds.

Beverage acidity can be adjusted to and maintained within a desired range by conventional methods such as the use of food grade acid buffers. Typically, beverage acidity within the above recited ranges is a balance between maximum acidity for microbial inhibition and optimum acidity for the desired beverage flavor. In some examples, the beverage compositions has a pH from about 2 to about 8, such as from about 2 to about 4.5 or about 2.7 to about 4.2.

Organic as well as inorganic edible acids may be used to adjust the pH of the beverage composition. The acids can be present in their undissociated form or as their respective salts, including potassium or sodium hydrogen phosphate, potassium or sodium dihydrogen phosphate salts. In some examples, the acids include citric acid, malic acid, fumaric acid, adipic acid, phosphoric acid, gluconic acid, tartaric acid, ascorbic acid, acetic acid, phosphoric acid, pyruvic acid or mixtures thereof. The acidulant can also serve as an antioxidant to stabilize beverage components. Examples of commonly used antioxidant include but are not limited to ascorbic acid, EDTA (ethylenediaminetetraacetic acid), and salts thereof.

E. Methods of Making Muscadine Compositions with Antioxidant Activity

Muscadine pomace extract compositions with antioxidant activity can be made by a variety of methods. For example, the compositions can be prepared by dissolving, dispersing, or otherwise mixing all components singularly or in suitable combinations together and in water where appropriate, and agitating the mixture with a mechanical stirrer until all of the ingredients have been solubilized or adequately dispersed. Separate solutions or mixtures may be combined. The final mixture can optionally be pasteurized or filled aseptically under appropriate process conditions to promote shelf-stability.

In some examples, a muscadine (*Vitis rotundifolia*) pomace extract having a polyphenol content of at least 2% is combined with resveratrol from a source other than muscadine wherein the resveratrol has a minimum purity of at least 5% (such as at least 10%, at least 20%, at least 30%, at least 40%, at least 50%, at least 60%, at least 70%, at least 80%, at least 90%, at least 95%, at least 98% or at least 99%) wherein a ratio of muscadine polyphenols to trans-resveratrol is in the range of 0.1/1 to 10/1 (weight to weight), for example 0.75 to 1, thereby producing a muscadine pomace extract and trans-resveratrol mixture with antioxidant activity. The disclosed methods can further include preparing the muscadine pomace extract prior to combining the muscadine pomace extract with trans-resveratrol.

In one particular example, the muscadine pomace extract is prepared by combining a bronze muscadine pomace extract with a purple muscadine pomace extract. In other examples, the muscadine pomace extract is prepared by extracting a mixture of bronze muscadine pomace and purple muscadine pomace simultaneously; in some instances the pomace is contained in whole purple muscadine grapes such that the extraction can be performed on a mixture of bronze pomace and purple muscadine grapes. The muscadine pomace extract can be prepared according to known methods such as crushing, pressing, extraction, filtering (several times), and concentration of the extract by vacuum evaporation followed by freezing. In one example, only water is utilized for the extraction process and no additional components (such as solvents, carriers, or preservatives) are added to the extract itself. The process is performed under conditions to preserve the polyphenolic compounds while reducing the presence of other molecules, for example, the majority of sugars. In other examples, ethanol or a mixture of ethanol and water are utilized for the extraction process. In particular examples, the extraction process can further include the use of enzymes for clarifying or facilitating extraction. For example, a blend of enzymes from *Aspergillus niger* or pectinase can be used for these purposes. Commercial examples include Scottzyme KS and ScottzymePEC5L from Scott Laboratories.

In other examples, the compositions are prepared by utilizing muscadine pomace extracts with a total phenol concentration of at least 2%. For example, commercially available muscadine extracts with a total phenol concentration of at least 2% can be used to prepare the disclosed compositions with antioxidant activity.

In a particular example, the composition with antioxidant activity is prepared by combining a muscadine pomace extract and resveratrol with an elderberry extract, a purple carrot extract, an excipient (such as glycerin, sorbitol, colloidal silicon dioxide, or a natural flavoring additive) or a combination thereof.

Another disclosed embodiment is a method of making an antioxidant composition by combining a muscadine (*Vitis rotundifolia*) pomace extract with resveratrol from a source other than muscadine, wherein a ratio of muscadine pomace extract polyphenols to trans-resveratrol is in the range of 0.1/1 to 10/1 (weight to weight), and the resulting composition has a polyphenol content of at least 2%. The muscadine pomace extract may optionally be concentrated prior to combining it with the resveratrol from a source other than muscadine. In some examples the muscadine pomace extract and resveratrol are combined with polyphenols from a source other than muscadine (such as a source of anthocyanins), for example from one or more of an extract of elderberry, black currant, blueberry, black raspberry, red raspberry, blackberry, bilberry, cloudberry, chokeberry, gooseberry, grape or purple carrot.

In particular embodiments, the method includes combining a mixture of bronze and purple muscadine pomace extract and elderberry fruit extract having a polyphenol content of at least 5% with a Japanese Knotweed root extract. In certain examples the Japanese Knotweed root extract is at least 98% resveratrol, and/or the muscadine pomace extract is a mixture of bronze and purple muscadine pomace extract. In some embodiments of the method the bronze and purple muscadine pomace extracts are combined or otherwise present in a ratio that ranges from 0.1 to 10.

In another embodiment, bronze and purple muscadine pomace extract are solvent extracted, either separately or together, to obtain a mixture of bronze and purple muscadine pomace extract containing solubilized ellagic acid, then the mixture of bronze and purple muscadine pomace extract are concentrated, for example to a solids content of at least 40%. The concentrated bronze and purple muscadine pomace extract mixture is combined with resveratrol from a source other than the muscadine pomace extract to obtain an antioxidant mixture, such that the ratio of muscadine pomace extract polyphenols to trans-resveratrol in the antioxidant mixture is in a range of 0.1/1 to 10/1 (weight to weight), and the resulting antioxidant composition has a polyphenol content of at least 2%.

In other embodiments of the method, the antioxidant composition is further combined with polyphenols (such as anthocyanins) from a source other than muscadine, for example by adding elderberry fruit extract to the antioxidant composition. In other embodiments the anthocyanins are from a source other than the pomace of the muscadine grape, for example anthocyanins from the juice of the muscadine grape introduced during the extraction process. In particular embodiments the components are combined so that the antioxidant composition includes at least 10% polyphenols, for example up to 35% polyphenols, such as 12-32%.

F. Methods and Kits for Inhibiting (for Example Preventing) Cellular Aging

The disclosed compositions have surprisingly synergistic lipophilic antioxidant activity. It is known that oxidative stress is a central mechanism underlying normal aging. It is also known that lipophilic antioxidants are capable of inhibiting various types of skin damage. Based on these observations, methods are disclosed for inhibiting cellular aging, for example by inhibiting or reducing free radical production or activity. In one example, a dose of the composition is administered to a subject in need of antioxidant activity and the dose is sufficient to inhibit or reduce one or more processes associated with cellular aging, such as free radical formation or activity in the subject.

The composition is also useful to treat any disorder associated with oxidative stress. The present extracts and combined compositions can be used to reduce, prevent or treat oxidative stress associated with the pathogenesis of chronic inflammatory diseases such as diabetes, cancer, atherosclerosis and other cardiovascular disease as well as with degenerative diseases of the central nervous system or brain, such as Alzheimer's disease and Parkinson's disease.

Some embodiments of the methods improve skin quality by inhibiting or reducing free radical formation or activity in a skin cell by applying a solution or topical ointment containing a muscadine pomace extract either alone or in combination with additional active ingredients, including without being limited to resveratrol. In one example, the solution or topical ointment includes a disclosed muscadine pomace extract without resveratrol. In another example, the solution or topical ointment includes both a disclosed muscadine pomace extract and resveratrol, such as a muscadine pomace extract with a ratio of muscadine polyphenols to resveratrol of about 0.75 to 1 (weight to weight). In yet other examples, the composition includes polyphenols (such as anthocyanins) from a source other than muscadine, for example from elderberry fruit extract. The method can be performed by a clinician or other healthcare provider, or can be designed for home use. The method can reduce the appearance of skin changes associated with aging, visibly reduce human skin wrinkles, and improve the textural quality of skin. Compositions and kits for improving skin quality are also provided that can include a disclosed composition (including oral or topical) with antioxidant activity or muscadine extract and one or more additional anti-aging compositions, such as one or more additional antioxidants.

Muscadine pomace extract compositions may be included in skin quality improvement kits for use in the home or by a clinician such as a physician or aesthetician. The kit can include applicators to apply the composition to skin, and instructions for use. The instructions can be written or in a digital formal (such as a videotape, DVD or CD) for use with electronic devices such as computers, CD players, mp3 players or DVD players and the like. In another example, the kit is suitable for use in the home. In some examples, the kit includes the muscadine composition and one or more additional anti-aging compounds, such as another antioxidant (e.g., vitamin C, vitamin E, selenium and/or beta-carotene), either in two separate containers or as a single composition in a single container.

G. Compositions with a Pharmaceutical Carrier

The disclosed muscadine pomace extracts and compositions can be useful for inhibiting one or more oxidative processes, such as free radical formation associated with cellular events such as cellular aging. The compositions can include a pharmaceutical carrier and at least one disclosed muscadine pomace extract either alone or in combination with resveratrol from a source other than muscadine. In some embodiments the composition also contains a supplemental source of polyphenols from other than muscadine. The pharmaceutical carrier can be for pharmaceutical or non-pharmaceutical uses, for example a use that may or may not require regulatory approval prior to sale for a particular purpose, such as a drug. However, a "pharmaceutical composition" as used herein refers to a composition that contains a pharmaceutically compatible carrier. Suitable pharmaceutical carriers are described in more detail in the incorporated U.S. patent application Ser Nos. 13/056,536; 13/056,559; and 13/784,566.

H. Administration of Disclosed Extracts and Compositions

In a particular example, a composition is administered orally to a mammalian subject, such as a human, in the form of a non-beverage food, a beverage or a dietary supplement. In another example, a composition is administered topically to a skin surface of a mammalian subject, such as a human.

The therapeutically effective amount of the agents administered can vary depending upon the desired effects and the subject to be treated. In one example, the method includes daily administration of at least 1 mg of the composition to the subject (such as a human subject). For example, a human can be administered at least 1 g or at least 10 g of the composition daily, such as 1 g to 5 g daily, 5 g to 10 g daily, for example 7 g daily. In one example, the subject is administered at least 5 g of the composition including muscadine pomace extract and resveratrol. In other examples, the subject is administered at least 6.3 g orally of such composition. The dosage can be administered in divided doses (such as 2, 3, or 4 divided doses per day), or in a single dosage daily.

In particular examples, the subject is administered the therapeutic composition on a multiple daily dosing schedule, for example on at least two consecutive days, 10 consecutive days, and so forth, and may continue for a period of weeks, months, or years. In one example, the composition is administered daily for a period of at least 30 days, such as at least 2 months, at least 4 months, at least 6 months, at least 12 months, at least 24 months, or at least 36 months.

The subject matter of the present disclosure is further illustrated by the following non-limiting Examples.

EXAMPLES

Example 1

Determination of Ellagic Acid Solubility in Muscadine Pomace Extracts

This example illustrates the effects of various specific ratios of bronze to purple pomace extracts on ellagic acid solubility, in both a non-concentrated and a concentrated extract. The mixture of bronze and purple extract increases the ellagic acid solubility.

Separate fermented bronze and purple pomace extracts were heated and then mixed in the ratios provided in Table 1 at a total volume of 100 ml.

TABLE 1

Various Ratios of Bronze/Purple Pomace extracts at 1× concentration

| Bronze (mls) | Purple (mls) |
|---|---|
| 75 | 25 |
| 65 | 35 |
| 50 | 50 |
| 25 | 75 |

The resulting extract mixtures were at a 1× concentration since no concentration of the separate bronze and purple pomace extracts had taken place. A 1× concentration typically contained about a 2% solids solution (100 grams of solution equal to 2 grams of dry extract). Approximately 20 milliliters of each ratio was transferred into a respective glass test tube and capped with foil. Samples were heated for 30 minutes at 85° C., then removed from the heat source and allowed to come to room temperature. Samples were then filtered through 0.45 µm PTFE filter w/GMF and analyzed via HPLC/MS to determine their content of ellagic acid. Separate bronze and purple muscadine pomace extracts were also analyzed, through the same process, to determine the baseline values of ellagic acid in both the bronze and purple pomace extracts and to determine the content of anthocyanins in the purple pomace extract. The total area of ellagic acid in the samples was then determined by reverse phase HPLC with a UV-VIS detection at 254 nm in tandem with a Ion-Trap mass detector, using extracted ion chromatogram (EIC) at [M-H]⁻= 301 amu.

To prepare various ratios of bronze/purple pomace extracts at 40% solids, separate bronze and purple muscadine pomace extracts at 1× were dried down into a powder form and re-constituted in water to produce a liquid containing 40% solids. These two separate solutions were then mixed into various ratios according to weight (wt) rather than volume. The various ratios evaluated are provided in Table 2A and 2B.

TABLE 2A

Determination of ellagic acid solubility in various Bronze/Purple extract ratios at 1× concentration

| | Pre-Analysis Conditions (non-filtered) Heat Extract @ 85° C./30 mins. Allow Cool R.T. (1 hour)/Filter/Analyze | | | % Increase Ellagic Acid |
|---|---|---|---|---|
| Sample ID | Ellagic Acid Relative µg/ml Experimental | Ellagic Acid Relative ug/ml Expected | Anthocyanins Relative µg/ml Extrapolated | Relative µg/ml Experimental vs. Expected |
| Bronze Extract @ 1× | 29.53 | | | |
| Purple Extract @ 1×) | 77.81 | | 472.50 | |
| 25:75 Purple/Bronze Ratio @ 1× | 43.43 | 41.60 | 118.12 | 4.40 |
| 35:65 Purple/Bronze Ratio @ 1× | 51.11 | 46.43 | 165.37 | 10.07 |
| 50:50 Purple/Bronze Ratio @ 1× | 58.59 | 53.67 | 236.25 | 9.16 |
| 75:25 Purple/Bronze Ratio @ 1× | 72.23 | 65.74 | 354.37 | 9.87 |

TABLE 2B

Determination of ellagic acid solubility in various Bronze/Purple extract ratios at approximately 20× concentration or 40% solids level

| | Pre-Analysis Conditions (non-filtered) Heat Extract @ 85° C./30 mins. Allow Cool R.T. (1 hour)/Filter/Analyze | | | % Increase Ellagic Acid Relative |
|---|---|---|---|---|
| Sample ID | Ellagic Acid Relative ug/ml Experimental | Ellagic Acid Relative ug/ml Expected | Anthocyanins Relative ug/ml Extrapolated | ug/ml Experimental vs. Expected |
| Bronze Extract @ ~40% solids | 3.00 | | | |
| Purple Extract @ ~40% solids | 26.25 | | 981.42 | |
| 2.25:1 Bronze/Purple Ratio ~40% solids | 12.19 | 10.15 | 301.97 | 20.13 |
| 2:1 Bronze/Purple Ratio ~40% solids | 13.29 | 10.75 | 327.14 | 23.66 |
| 1:1 Bronze/Purple Ratio ~40% solids | 20.01 | 14.62 | 490.71 | 36.80 |

Approximately 10 milliliters of each ratio was transferred into a respective glass test tube and capped with foil. Samples were heated for 30 minutes at 85° C., then removed from the heat source and allowed to come to room temperature. Samples were then filtered through a 0.45 μm PTFE filter w/GMF and analyzed via HPLC/MS to determine their content of ellagic acid. Separate bronze and purple muscadine pomace extracts were also analyzed, through the same process, to determine the baseline values of ellagic acid in both bronze and purple muscadine pomace extracts and to determine the content of anthocyanins in the purple muscadine pomace extract. Validated test method C2505 was used to determine the total area of ellagic acid in the samples, in tandem with a Ion-Trap mass detector using extracted ion chromatogram (EIC) at $[M-H]^-=301$ amu.

Mixing the purple with the bronze muscadine pomace extract increased solubility of solubility of ellagic acid in the mixture. These studies found that a ratio of 65% to 35% bronze to purple pomace extract (volume to volume) was sufficient to promote the maximum solubility of ellagic acid in a mixture of the two pomace extracts at the 1× concentration level. Further, at a 40% solids level, the solubility of ellagic acid continued to increase as the content of purple muscadine pomace extract increased in the mixture. These findings suggest that at a 40% solids level, greater amounts of ellagic acid existed in the solid form, so a higher content of purple pomace extract is useful to fully solubilize all the ellagic acid present in the mixture. These studies also suggest that anthocyanins, such as those contained in the purple muscadine pomace extract, influence the solubility of ellagic acid contained within the bronze muscadine pomace extract.

Example 2

Anti-Aging Dietary Supplement and Preparation Thereof

Dietary supplements that can be consumed to prevent or inhibit one or more processes associated with cellular aging are disclosed in WO 2010/014870 and WO 2010/014873, which are incorporated by reference.

The dietary supplement includes instructions regarding dosages. For example, the instructions can indicate that 5 milliliters of a liquid supplement (approximately one teaspoon) can be taken daily before a meal and used as an anti-aging supplement for inhibiting one or more processes associated with cellular aging.

Example 3

Antioxidant Capacity of Muscadine Pomace Extract and Japanese Knotweed Root Extract Mixture This example demonstrates the improved antioxidant capacity of a mixture of Japanese knotweed extract and muscadine pomace extract as measured by an Oxygen Radical Absorbance Capacity (ORAC) assay.

The antioxidant capacity of two botanical extracts separately or in combination was evaluated using the ORAC assay. This assay has been used to measure the antioxidant capacity of a wide range of foods and beverages and is the basis for the data contained in the USDA ORAC database. Both hydrophilic antioxidant capacity and lipophilic antioxidant capacity can be measured by this test.

The following samples were analyzed: (1) Dried/powdered Japanese knotweed root extract standardized to a minimum 98% trans-resveratrol (actual content was 100% trans-resveratrol); (2) Dried/powdered Muscadine pomace extract (2:1 ratio of bronze to purple pomace) containing 14.4% total polyphenol content; and (3) Mixture of the above dried/powdered Japanese knotweed and dried/powdered muscadine pomace extracts in a 1:5.36 (wt:wt) ratio (total polyphenol content was 27.5% of mixture and the ratio of muscadine polyphenols to trans-resveratrol was 0.75 to 1. Hydrophilic, lipophilic and total ORAC values were measured (total ORAC value is the sum of the hydrophilic and lipophilic values) and the results are expressed as μmole Trolox Equivalents per milligram polyphenol (μmoleTE/mg polyphenol). The results are shown in Table 3.

TABLE 3

Hydrophilic, lipophilic and total ORAC values for Samples 1-3 as expressed as μmoleTE/mg polyphenol

| Sample Extract | ORAC$_{hydrophilic}$ | ORAC$_{lipophilic}$ | ORAC$_{total}$ |
|---|---|---|---|
| (1) Japanese knotweed (100% resveratrol) | 29.85 | 1.46 | 31.31 |
| (2) Muscadine pomace (14.4% polyphenols) | 9.69 | 0.06 | 9.74 |
| (3) Mixture—predicted additivity | 21.19 | 0.86 | 22.05 |
| (3) Mixture—actual value | 21.83 | 4.35 | 26.18 |

As displayed in Table 3, the measured hydrophilic ORAC value of the mixture is similar to the predicted value based on the additive effects of the two extracts. However, the measured lipophilic ORAC value of the mixture is five times greater than the predicted additive value resulting in a 20% increase in the total ORAC value. Table 4 shows the results expressed as ORAC value per gram of material (versus per mg polyphenol as shown in Table 3). As displayed in Table 4, the synergistic effects of the muscadine pomace extract and Japanese knotweed root extract mixture in producing lipophilic antioxidant capacity are maintained when values are expressed as ORAC per gram of material:

TABLE 4

Hydrophilic, lipophilic and total ORAC values for Samples 1-4
as expressed as ORAC value per gram of material

| Extract Sample | $ORAC_{hydrophilic}$ | $ORAC_{lipophilic}$ | $ORAC_{total}$ |
|---|---|---|---|
| (1) Japanese knotweed (100% resveratrol) | 29,852 | 1,457 | 31,309 |
| (2) Muscadine pomace (14.4% polyphenols) | 1,356 | 8 | 1,364 |
| (3) Mixture—predicted additivity | 5,830 | 236 | 6065 |
| (3) Mixture—actual value | 6,003 | 1,197 | 7200 |

Example 4

Effect of Elderberry Fruit Extract on Ellagic Acid Solubility in Muscadine Pomace Extract As shown in Example 1, the addition of purple pomace extract to bronze pomace extract enhanced the solubility of ellagic acid contained within the bronze pomace extract. This effect was considerably greater in extracts that were concentrated to the 40% solids level (versus 2% solids level). These findings suggested that the addition of anthocyanins from the purple muscadine pomace extract was beneficial for increasing ellagic acid solubility in bronze muscadine pomace extracts containing high concentrations of ellagic acid.

Elderberry fruit extract contains significant amounts of anthocyanins (but no ellagic acid) and thus experiments were performed to determine whether the soluble ellagic acid content within a muscadine pomace extract (bronze and purple pomace mixture) is influenced by the addition of anthocyanins from elderberry fruit extract. This example shows that soluble ellagic acid content within a muscadine pomace extract is significantly increased by the addition of elderberry fruit extract presumably owing to its anthocyanin content.

Ellagic acid concentrations were measured in (1) dried powdered muscadine pomace extract (2:1 ratio of bronze to purple pomace) and (2) a mixture of the above muscadine pomace extract and dried powdered elderberry fruit extract (containing 6.5% anthocyanins) in a 1:1.86 ratio (wt:wt). Solutions of each sample were prepared at various concentrations to provide 40%, 20%, 10%, and 2% solids. Each solution was heated for 30 minutes at 85° C., removed from the heat source and allowed to reach to room temperature (complete by 1 hour). Samples were then filtered through 0.45 µm PTFE filter w/GMF and analyzed via HPLC/MS to determine their content of soluble ellagic acid. Total area of ellagic acid was assessed by reverse phase HPLC with UV-VIS detection at 254 nm in tandem with a Ion-Trap mass detector, using extracted ion chromatogram (EIC) at [M-H]⁻= 301 amu. The results are shown in Table 5.

TABLE 5

Effect of elderberry fruit extract (anthocyanins)
on soluble ellagic acid content
in muscadine pomace extract

| | Soluble ellagic acid content (µg/ml) | | | |
|---|---|---|---|---|
| % solids | Muscadine pomace extract (measured) | Muscadine pomace extract/ elderberry fruit extract mixture (expected) | Muscadine pomace extract/ elderberry fruit extract mixture (measured) | % increase over predicted |
| 40 | 2,221.88 | 776.88 | 1,155.81 | 48.78 |
| 20 | 1,075.90 | 376.19 | 520.96 | 38.48 |
| 10 | 411.25 | 143.79 | 238.34 | 65.76 |
| 2 | 74.81 | 26.16 | 39.14 | 49.62 |

These results clearly illustrate that the muscadine pomace extract/elderberry fruit extract contained considerably greater amounts (40-65% more) of soluble ellagic acid than that predicted by the contribution of muscadine pomace extract. Although the muscadine pomace extract was prepared from a mixture of bronze and purple pomace extracts and thus contained anthocyanins from the purple pomace (thus promoting ellagic acid solubility), the addition of anthocyanins from a source other than muscadine (elderberry fruit extract) appeared to augment ellagic acid solubility even further.

Confirmation of this idea was sought by measuring the absolute value of total ellagic acid in the muscadine pomace extract to learn what portion of the total ellagic acid content was soluble under the conditions described above. To determine the absolute value of total ellagic acid contained within the samples, each dried powder (samples 1 and 2) was dissolved in DMSO and their ellagic acid contents were assessed as described above (total area of ellagic acid was measured by reverse phase HPLC with UV-VIS detection at 254 nm in tandem with a Ion-Trap mass detector, using extracted ion chromatogram (EIC) at [M-H]⁻=301 amu). The following tables (6 and 7) show that the percentage of total ellagic acid that becomes soluble was enhanced by both endogenous muscadine pomace anthocyanins and by the addition of exogenous anthocyanins from elderberry fruit extract.

TABLE 6

Effect of muscadine pomace anthocyanins
on the solubility of total ellagic acid in muscadine pomace extract

| | Ellagic acid content (µg/ml) | | |
|---|---|---|---|
| % solids | Muscadine pomace extract (total content) | Muscadine pomace extract (soluble content) | % of total ellagic acid that is soluble |
| 40 | 4,360.00 | 2,221.88 | 50.96 |
| 20 | 2,180.00 | 1,075.90 | 49.35 |
| 10 | 1,090.00 | 411.25 | 37.73 |
| 2 | 218.00 | 74.81 | 34.32 |

Table 6 shows that the endogenous anthocyanins in the muscadine pomace extract (from the purple pomace) enhanced the percentage of total ellagic acid that becomes solubilized. The increasing levels of solids content are attended by increasing content of endogenous anthocyanins and thus, the percentage of soluble ellagic acid rose from 34% to 50% of the total ellagic acid content contained within the muscadine pomace extract. Nevertheless, a maximum of only 50% of the total ellagic acid content of the muscadine pomace extract was solubilized by the endogenous anthocyanin content from the purple pomace.

TABLE 7

Effect of elderberry fruit extract (anthocyanins) on the solubility of total ellagic acid in muscadine pomace extract

| | Ellagic acid content (μg/ml) | | |
|---|---|---|---|
| % solids | Muscadine pomace extract/elderberry fruit extract mixture (total content) | Muscadine pomace extract/elderberry fruit extract mixture (soluble content) | % of total ellagic acid that is soluble |
| 40 | 1,524.47 | 1,155.81 | 75.82 |
| 20 | 762.24 | 520.96 | 68.35 |
| 10 | 381.12 | 238.34 | 62.54 |
| 2 | 76.22 | 39.14 | 51.35 |

Table 7 shows that the inclusion of additional and exogenous anthocyanins from elderberry fruit extract greatly enhanced the solubility of the ellagic acid contained within the muscadine pomace extract. As the levels of solids were increased, the content of total anthocyanins (endogenous and exogenous) also increased and the percentage of soluble ellagic acid rose from 51% to 75% of the total ellagic acid content of the muscadine pomace extract. Moreover, the addition of exogenous anthocyanins from elderberry fruit extract enhanced the solubility of ellagic acid at all levels of solids content when compared to the muscadine pomace extract alone. Indeed, at the 40% solids level, the addition of exogenous anthocyanins from elderberry extract enabled the solubilization of 75% of the total ellagic acid content whereas the endogenous anthocyanins from the purple pomace solubilized only 50% of the total ellagic acid content. In conclusion, although the anthocyanins found in purple muscadine pomace enhance ellagic acid solubility of the muscadine pomace extract, additional anthocyanins from a source other than muscadine provide further surprising increases in ellagic acid solubility.

Example 5

Extraction from Pomace Contained in a Whole Grape

Previous examples have disclosed the use of muscadine pomace (such as pomace-only wherein the juice comprises less than 1% of the weight of the pomace-only). In those examples the muscadine pomace extracts are derived from combining bronze muscadine pomace extract and purple muscadine pomace extract in various ratios. The bronze muscadine pomace extract and purple muscadine pomace extract may be prepared separately before combining them at particular ratios or the bronze muscadine pomace and purple muscadine pomace may be combined at various ratios and then extracted simultaneously.

The process disclosed in the present example is similar, except the purple muscadine pomace can be contained in a whole muscadine grape that either has all its original juice, or from which no more than 5% or 10% of the juice content has been extracted. The whole purple muscadine grape containing a purple muscadine pomace component is therefore used instead of purple muscadine pomace-only. Although the whole bronze muscadine grape may also be substituted for bronze muscadine pomace, in the present example the whole bronze muscadine grape is not used, but only the bronze pomace is used. Hence the starting materials in this example are bronze muscadine pomace-only, purple muscadine pomace-only and whole purple muscadine grapes. The whole purple muscadine grapes (which include the partially crushed or compressed whole purple muscadine grapes) can be added to bronze muscadine pomace-only or to a mixture of bronze and purple muscadine pomaces-only. The mixture of bronze and purple muscadine pomaces-only can be extracted simultaneously with the whole purple grapes. When the whole purple muscadine grapes are mixed with the bronze muscadine pomace-only for simultaneous extraction of those two starting materials, the resulting extract can be added to purple muscadine pomace-only extract again in various ratios. It is believed that the anthocyanins found in the whole purple muscadine grape (but not the whole bronze muscadine grape) contribute additional anthocyanins to the extract that unexpectedly solubilize the ellagic acid in the extract to help retain the full polyphenol content of the starting materials.

In other embodiments, a colored (containing anthocyanins) fruit processing waste stream such as blueberry skins can be mixed with bronze muscadine pomace or to a mixture of bronze and purple muscadine pomaces-only in addition to or as a substitute for the whole purple muscadine grapes. The blueberry skins are part of a "waste-stream" in this example if they are a by-product of the production of blueberry juice or blueberry puree. The blueberry skins would typically be discarded as waste from the blueberry juice and/or puree production process but they can instead be used as an additional source of anthocyanins for the solubilization of ellagic acid in the muscadine pomace extract. Although this example discloses the use of a colored fruit processing waste stream (such as blueberry skins), any source of anthocyanins other than purple muscadine grapes and/or purple muscadine pomace can be used (such as anthocyanin-enriched fruit juice concentrates or extracts). Fruit juice concentrate from colored fruits (such as black, red, blue, or purple fruits) is a particularly rich source of anthocyanins that can be extracted along with the bronze and purple muscadine pomace extract to desirably enhance ellagic acid solubility in the extract.

A noted previously, in the combined solvent extracts the ratios of bronze muscadine pomace to purple muscadine pomace range from 10:1 (weight to weight) to 1:10 (weight:weight).

In some examples, the combined solvent extracts contain extracts comprising, or are prepared from a ratio of whole purple muscadine grapes to bronze muscadine pomace that ranges from 1:5 to 1:12 (weight:weight).

In other examples, the solvent extracts are comprised of or are prepared from a ratio of whole purple muscadine grapes to a mixture of bronze and purple muscadine pomaces that ranges from 1:7 to 1:16 (weight:weight).

The ratio of anthocyanins to ellagic acid in the starting materials (bronze muscadine pomace-only, purple muscadine pomace-only, and whole purple muscadine grapes) ranges from 0.5:1 to 5:1 (weight:weight).

All of the other steps such as extraction with heated water, treatment with enzymes, filtration, fermentation, concentration, and polyphenol content can be the same as in the other extraction methods described in prior examples herein.

Example 6

Comparison of Ellagic Acid Solubility in Extracts Derived from (A) a Mixture of Bronze/Purple Pomace-Only and (B) Whole Purple Grapes and Bronze Muscadine Pomace-Only Mixed with Purple Pomace-Only The presence of ellagic acid in muscadine grapes is unique among grapes (*Vitus* species). As described in Example 1, the addition of purple muscadine pomace-only extract to bronze muscadine pomace-only extract enhanced the solubility of ellagic acid. It has been found that anthocyanins (found in purple, but not bronze, muscadine grapes/pomace) mediated part or all of this effect. As shown in Example 1, a ratio of 2:1 bronze:purple muscadine pomace-only extracts was sufficient to produce the maximum increase in solubility of ellagic acid in extracts at 1× concentration (2% solids). Experiments were thus performed to determine whether the addition of whole or partially crushed whole purple muscadine grapes (instead of purple pomace-only) to bronze pomace-only likewise promoted ellagic acid solubility in muscadine extracts. The term "pomace-only" refers to grape pomace of a grape from which at least 95% of the juice content has been removed, while a "whole grape" refers to a grape that contains at least 90% (in some examples at least 95%) of its original juice content.

Two muscadine pomace extracts (A and B) were prepared in a pilot-scale trial. For extract A, bronze muscadine pomace-only and purple muscadine pomace-only were extracted separately in hot water and then mixed into a 2:1 (weight:weight) ratio (bronze muscadine pomace-only extract:purple muscadine pomace-only extract). The combined extract was then filtered, fermented, refiltered and concentrated to 40% solids as described previously. Extract B was prepared by extracting bronze muscadine pomace-only plus whole purple grapes in a 8.7:1 (weight:weight) ratio (bronze pomace-only:whole purple grapes) and separately extracting purple muscadine pomace-only and then mixing the resulting extracts in a 15:1 (weight:weight) ratio such that the ratio of bronze muscadine pomace-only extract, purple muscadine pomace-only extract, and whole purple muscadine grape extract was 13.8:1:1.6. On a weight basis, whole purple grapes yield roughly 25% pomace and thus extract B can also be described as being a mixture of bronze muscadine pomace-only and purple muscadine pomace-only extracts in a 10:1 ratio (bronze:purple, weight to weight). Extract B was filtered, fermented, refiltered and concentrated to 40% solids as described for extract A.

Samples of extracts A and B were dried down (lyophilized) to a powder form. To determine total ellagic acid content of each extract, the powdered samples were dissolved in DMSO and analyzed via HPLC/MS (validated test method C2505). Total area of ellagic acid was assessed by reverse phase HPLC with UV-VIS detection at 254 nm in tandem with a Ion-Trap mass detector, using extracted ion chromatogram (EIC) at [M-H]$^-$=301 amu. To determine the content of soluble ellagic acid, solutions of extracts A and B were prepared at various concentrations to provide 40% and 2% solids. Each solution was heated for 30 minutes at 85° C., removed from the heat source and allowed to reach to room temperature (complete by 1 hour). Samples were then filtered through 0.45 µm PTFE filter w/GMF and analyzed as above. The results are shown in Tables 8 and 9.

TABLE 8

Soluble ellagic acid content of extracts A and B at 2% solids level
Ellagic acid content (µg/ml)

| | Total ellagic acid content | Soluble ellagic acid content | % of total ellagic acid that is soluble |
|---|---|---|---|
| Extract A (2:1 bronze pomace-only:purple pomace-only, weight:weight) | 114.90 | 61.85 | 53.83 |

TABLE 8-continued

Soluble ellagic acid content of extracts A and B at 2% solids level
Ellagic acid content (µg/ml)

| | Total ellagic acid content | Soluble ellagic acid content | % of total ellagic acid that is soluble |
|---|---|---|---|
| Extract B (13.8:1:1.6 bronze pomace-only:purple pomace-only:whole purple grapes, weight:weight:weight) | 97.35 | 55.27 | 56.77 |

TABLE 9

Soluble ellagic acid content of extracts A and B at 40% solids level
Ellagic acid content (µg/ml)

| | Total ellagic acid content | Soluble ellagic acid content | % of total ellagic acid that is soluble |
|---|---|---|---|
| Extract A (2:1 bronze pomace-only:purple pomace-only, weight:weight) | 2,620.0 | 1,936.2 | 73.89 |
| Extract B (13.8:1:1.6 bronze pomace-only:purple pomace-only:whole purple grapes, weight:weight:weight) | 2,218.6 | 1,645.1 | 74.15 |

These results show that the ellagic acid solubility of extracts A and B are substantially identical at both concentrations (2% and 40% solids). This was not expected because the ratio of bronze to purple muscadine pomace extracts is 2:1 in extract A versus 10:1 (including the contribution of pomace by the whole grapes) in extract B. Thus, the addition of whole purple muscadine grapes as a starting material significantly enhances ellagic acid solubility to a greater degree than is predicted in Example 1.

As shown in Example 1, a mixture of pomace-only extracts at the 1× concentration (2% solids) at a ratio of bronze pomace-only extract to purple pomace-only extract greater than 2:1 (such as 3:1 or as shown in the example 25:75 Purple/Bronze Ratio), produced negligible increases (4.4%) in ellagic acid solubility. Similar increases (about 10%) in ellagic acid solubility were observed at bronze:purple ratios of 2:1, 1:1, and 1:2 suggesting that maximal increases in ellagic acid solubility required at least a 2:1 ratio of bronze to purple pomace-only extracts (or at least 1 part purple to 2 parts bronze). The current experiments demonstrate that when the anthocyanins are introduced in the form of whole purple muscadine grapes (versus purple pomace-only), maximal increases in ellagic acid solubility can be achieved at a ratio of 10:1 to bronze:purple muscadine pomace (or 1 part purple to 10 parts bronze). This is further surprising because virtually all (>95%) the anthocyanin content within purple muscadine grapes is located in the skin, a constituent of the pomace. The current experiment thus surprisingly finds that the addition of even very small amounts of additional anthocyanins in the form of whole grapes greatly improves the ellagic acid solubility of muscadine pomace-only extracts.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of producing a muscadine extract, comprising:
combining (a) a bronze muscadine pomace-only solvent extract with (b) a purple muscadine pomace-only solvent extract and a whole purple muscadine grape solvent extract;
filtering (a) and (b) either separately prior to combining (a) and (b) or together after combining (a) and (b); and
fermenting (a) and (b) before or after the filtering to remove extracted sugars.

2. The method of claim 1, wherein the method comprises combining (a) and (b) in a ratio that ranges from 0.1 to 10 (weight to weight) and the muscadine extract has a polyphenol content of at least 2%.

3. The method of claim 2, wherein the muscadine extract has a total polyphenol content of at least about 4%.

4. The method of claim 2, wherein the ratio of (a) to (b) ranges from 0.3 to 3 (weight:weight).

5. The method of claim 1, wherein combining (a) and (b) comprises solvent extracting purple muscadine pomace-only and solvent extracting bronze muscadine pomace-only to provide a pomace-only solvent extract, then combining the pomace-only solvent extract with solvent extract from the bronze muscadine pomace-only and whole purple muscadine grapes.

6. The method of claim 1, wherein combining (a) and (b) comprises solvent extracting the bronze muscadine pomace-only, the purple muscadine pomace-only, and the whole purple muscadine grape prior to combining (a) and (b) to produce the muscadine extract having a polyphenol content of at least 2%.

7. The method of claim 1, wherein the solvent extract is a water extract.

8. The method of claim 1, comprising fermenting (a) and (b) after the filtering.

9. The method of claim 1, further comprising concentrating (a) and (b) so that each or both of (a) and (b) comprise 20% to 50% solids in a liquid.

10. The method of claim 9, wherein each or both of (a) and (b) comprise about 40% solids in a liquid.

11. The method of claim 9, wherein concentrating (a) and (b) follows filtering (a) and (b).

12. The method of claim 11, wherein the muscadine extract comprises about 40% solids in a liquid.

13. The method of claim 1, further comprising adding an excipient or additional ingredient to the muscadine extract.

14. The method of claim 13, further comprising adding resveratrol or anthocyanin to the muscadine extract.

15. A composition made by the method of claim 1.

16. The composition of claim 15, wherein the ratio of (a) to (b) ranges from 0.1 to 10 (weight to weight) and the muscadine extract has a polyphenol content of at least 2%.

17. The method of claim 1, wherein producing the muscadine extract comprises solvent extracting whole purple muscadine grapes and bronze muscadine pomace-only in a ratio that ranges from 1:5 to 1:12 (weight:weight).

18. The method of claim 1, wherein producing the muscadine extract comprises solvent extracting a mixture of starting materials that contains a ratio of anthocyanin to ellagic acid that ranges from 0.5:1 to 5:1 (weight:weight).

19. A method of producing a muscadine extract, comprising:
combining (a) a bronze muscadine pomace-only solvent extract with (b) a purple muscadine pomace-only solvent extract and a whole purple muscadine grape solvent extract;
filtering (a) and (b) either separately prior to combining (a) and (b) or together after combining (a) and (b); and
fermenting (a) and (b) before or after the filtering to remove extracted sugars;
wherein combining (a) and (b) comprises combining bronze muscadine pomace-only and purple muscadine pomace-only and solvent extracting the bronze pomace-only and purple pomace-only simultaneously, then adding whole purple muscadine grape extract.

20. A muscadine extract composition comprising (a) a bronze muscadine pomace-only solvent extract and (b) purple muscadine pomace-only solvent extract and purple muscadine whole grape solvent extract, wherein a ratio of (a) to (b) ranges from 0.1 to 10 (weight to weight) and the muscadine extract has a polyphenol content of at least 2%, and the muscadine extract is filtered and/or fermented.

21. The composition of claim 20, wherein the composition is provided in a non-beverage food, a beverage, a dietary supplement or a cosmetic composition.

22. The composition of claim 20 wherein (a) and (b) together comprises 20 to 50% solids.

23. The composition of claim 20 wherein the composition comprises an anti-oxidant supplement.

24. The composition of claim 20, wherein the ratio of (a) to (b) ranges from about 0.3 to 3 (weight to weight).

25. The composition of claim 20, further comprising resveratrol or an anthocyanin from a source other than muscadine pomace.

26. The composition of claim 25, comprising the resveratrol.

27. The composition of claim 26, wherein the resveratrol is from Japanese knotweed extract.

28. The composition of claim 20 further comprising an anthocyanin from a source other than muscadine pomace.

29. The composition of claim 28, wherein the anthocyanin from the source other than muscadine pomace is from purple muscadine grape juice.

30. The composition of claim 28, wherein the anthocyanin is from a colored fruit.

31. The composition of claim 30 wherein the colored fruit comprises elderberry, blueberry, blackberry or raspberry.

32. The composition of claim 30, wherein the anthocyanin is from a fruit processing waste stream.

33. The composition of claim 20, formulated as a solid composition.

34. The composition of claim 33, wherein the solid composition comprises a powder, pill, tablet or capsule.

35. The composition of claim 20, comprising additional nutrients.

36. The composition of claim 35, wherein the additional nutrients are one or more vitamins or minerals.

37. The composition of claim 35, wherein the additional nutrients are one or more of iron, zinc, copper, calcium, phosphorous, niacin, thiamin, folic acid, pantothenic acid, iodine, vitamin A, vitamin C, vitamin B2, vitamin B3, vitamin B6, vitamin B12, vitamin D, vitamin E, and vitamin K.

38. The composition of claim 20, further comprising dietary fiber.

39. A method of producing a muscadine extract, comprising:
- combining (a) a bronze muscadine pomace-only solvent extract with (b) a purple muscadine pomace-only solvent extract and a whole purple muscadine grape solvent extract;
- filtering (a) and (b) either separately prior to combining (a) and (b) or together after combining (a) and (b); and
- fermenting (a) and (b) before or after the filtering to remove extracted sugars;
- wherein producing the muscadine extract comprises solvent extracting whole purple muscadine grapes and a mixture of bronze and purple muscadine pomace-only in a ratio that ranges from 1:7 to 1:16 (weight:weight).

* * * * *